US00PP17420P2

(12) United States Plant Patent
Zaias-Fast

(10) Patent No.: US PP17,420 P2
(45) Date of Patent: Feb. 20, 2007

(54) ***MICROSORIUM* PLANT NAMED 'VP005'**

(50) Latin Name: *Microsorium puncatatum*
Varietal Denomination: VP005

(76) Inventor: Magaly Zaias-Fast, 11068 NW. Third St., Miami Beach, FL (US) 33071

( * ) Notice: Subject to any disclaimer, the term of this patent is extended or adjusted under 35 U.S.C. 154(b) by 29 days.

(21) Appl. No.: 11/166,650

(22) Filed: Jun. 25, 2005

(51) Int. Cl.
*A01H 5/00* (2006.01)

(52) U.S. Cl. ..... Plt./379
(58) Field of Classification Search ..... Plt./379
See application file for complete search history.

*Primary Examiner*—Kent Bell

(57) ABSTRACT

A new cultivar of *Microsorium* plant named 'VP005' that is characterized by dark green curly fronds and a compact habit.

1 Drawing Sheet

Botanical classification: *Microsorium punctatum.*
Variety denomination: 'VP005'.

BACKGROUND OF THE INVENTION

The present invention relates to a new and distinct cultivar of *Microsorium* plant botanically known as *Microsorium punctatum* and hereinafter referred to by the cultivar name 'VP005'.

The new cultivar was discovered by the inventor in a cultivated area of Miami, Fla. in May of 2000. 'VP005' was discovered as a naturally occurring whole plant mutation of an unnamed *Microsorium punctatum* (not patented).

Asexual reproduction by tissue culture of the new cultivar 'VP005' was first done in June of 2003 in Renesse, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Microsorium* cultivar 'VP005'. These traits in combination distinguish 'VP005' as a new and distinct cultivar apart from other known existing varieties of *Microsorium.*

1. *Microsorium* 'VP005' exhibits curled frond margins.
2. *Microsorium* 'VP005' exhibits a compact habit.
3. *Microsorium* 'VP005' exhibits dark green fronds.

The new cultivar 'VP005' is distinguishable from the parent *Microsorium* plant by the following characteristics:

1. 'VP005' has darker fronds.
2. 'VP005' has frond margins that are curled.
3. 'VP005' has a more compact habit.

The closest comparison cultivar is *Microsorium* 'Cobra' (not patented). The new cultivar 'VP005' is distinguishable from 'Cobra' by the following characteristics:

1. 'VP005' has a more compact habit.

BRIEF DESCRIPTION OF THE DRAWING

The accompanying photograph illustrates the distinguishing traits of *Microsorium* 'VP005'. The photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Microsorium* cultivar named 'VP005'. Data was collected in Renesse, Netherlands from 2 year old glass greenhouse grown plants. The time of year was Winter. The average temperature was 22° Centigrade during the day and 20° Centigrade at night. The light level was natural outdoor light. Color determinations are in accordance with The Royal Horticultural Society Colour Chart 2001 edition, except where general color terms of ordinary dictionary significance are used. The growing requirements are similar to the species.

'VP005' has not been tested under all possible conditions and phenotypic differences may be observed with variations in environmental, climatic, and cultural conditions, however, without any variance in genotype.

Botanical classification: *Microsorium punctatum.*
Use: Ornamental perennial.
Plant type: Potted Plant.
Parentage: 'VP005' was discovered as a naturally occurring whole plant mutation of an unnamed *Microsorium punctatum.*
Vigor: Medium.
Growth habit: Upright.
Plant shape: Narrow inverted triangle.
Suitable container size: 12 cm.
Height: 41 cm. in height.
Width: 35 cm. in width.
Hardiness: USDA Zone 10.
Propagation: Tissue culture.
Crop time: From propagation, approximately 2 years are required to produce a finished plant.
Time to initiate roots: 14 days at 22 degrees Centigrade.
Time to produce a rooted cutting or liner: 56 days in the summer, 70 days in the winter.
Rhizomes: Dull, rough, 2.1 cm. in length between fronds and 0.6 cm in diameter, color N199B.
Stem: None, fronds grow directly from roots.

Frond:

*Shape.*—Flabellate to bifurcate.

*Aspect.*—Upright, curled and twisted at the top.

*Quantity.*—26 per plant.

*Length.*—31 cm. in length.

*Width.*—12.6 cm. in width.

*Apex.*—Bifurcate to multifurcate, heavily crinkled and twisted.

*Base.*—Narrow Cuneate.

*Texture.*—Smooth, leathery.

*Margin.*—Entire.

*Vein pattern.*—Forked.

*Young color* (*lower surface*).—143A to 144A.

*Young color* (*upper surface*).—143A to 144A.

*Mature color* (*lower surface*).143A.

*Mature color* (*upper surface*).—141A to 143A.

*Vein color* (*lower surface*).—146A.

*Vein color* (*upper surface*).—147B.

*Durability of fronds to stress.*—High.

Rachis: None, fronds simple.

Pinnea: None, fronds simple.

Flower: None observed, no spores observed.

Disease and pest resistance: Has not been observed.

It is claimed:

1. A new and distinct variety of *Microsorium* plant named 'VP005' as described and illustrated.

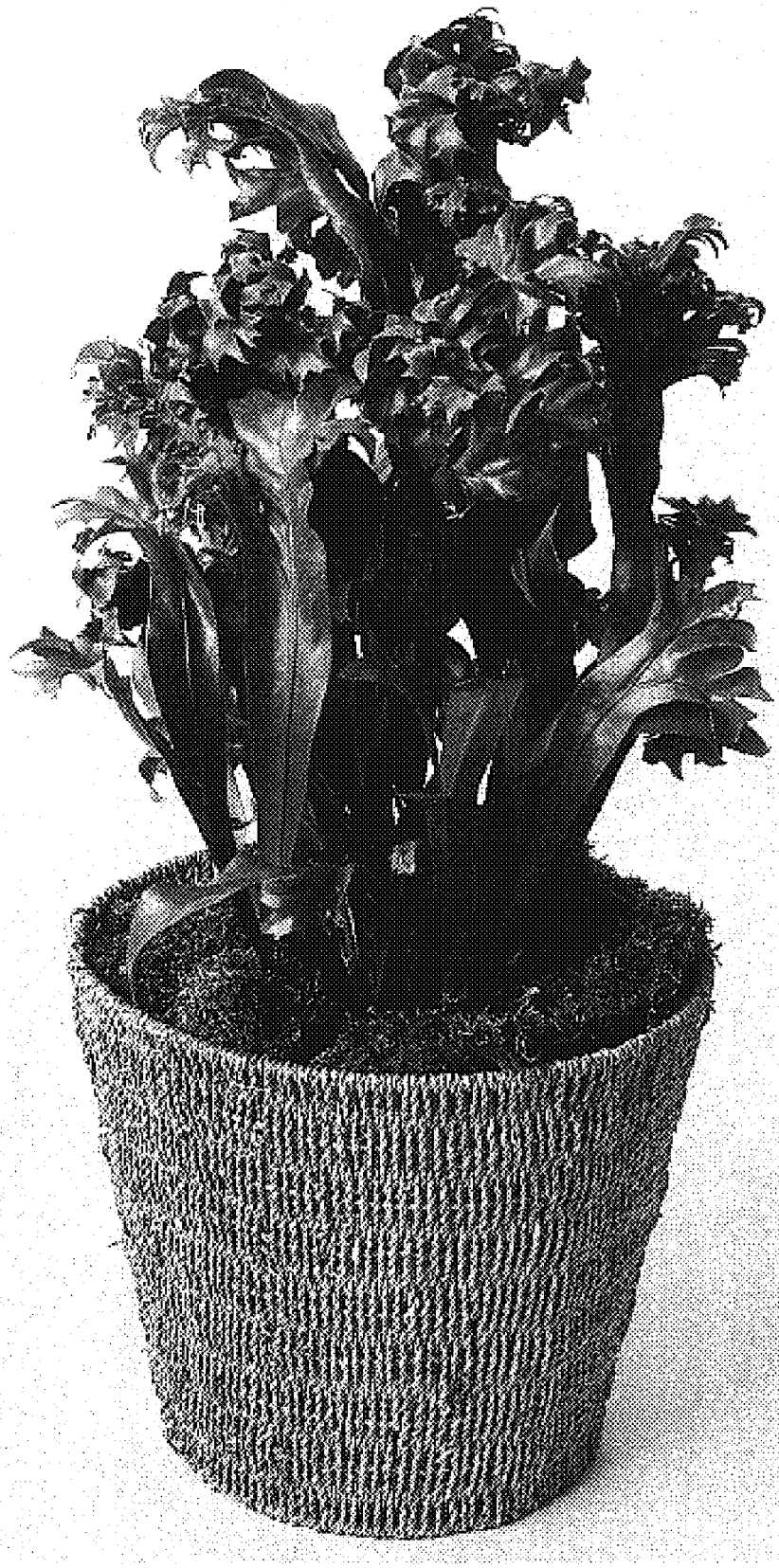

* * * * *